United States Patent
Scharf et al.

(10) Patent No.: US 9,504,395 B2
(45) Date of Patent: *Nov. 29, 2016

(54) DEVICE AND METHOD FOR THE GEOMETRIC DETERMINATION OF ELECTRICAL DIPOLE DENSITIES ON THE CARDIAC WALL

(71) Applicant: Christoph Scharf, Horgen, Zurich (CH)

(72) Inventors: Christoph Scharf, Zurich (CH); Gunter Scharf, Zurich (CH)

(73) Assignee: Christoph Scharf (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/886,449

(22) Filed: Oct. 19, 2015

(65) Prior Publication Data

US 2016/0038051 A1 Feb. 11, 2016

Related U.S. Application Data

(63) Continuation of application No. 13/946,712, filed on Jul. 19, 2013, now Pat. No. 9,192,318, which is a continuation of application No. 12/863,411, filed as application No. PCT/IB2009/000071 on Jan. 16, 2009, now Pat. No. 8,512,255.

(30) Foreign Application Priority Data

Jan. 17, 2008  (CH) .......................... 68/08

(51) Int. Cl.
| | |
|---|---|
| *A61B 5/04* | (2006.01) |
| *A61B 5/0402* | (2006.01) |
| *A61B 5/042* | (2006.01) |

(Continued)

(52) U.S. Cl.
CPC ....... *A61B 5/04012* (2013.01); *A61B 5/02028* (2013.01); *A61B 5/0402* (2013.01); *A61B 5/044* (2013.01); *A61B 5/04005* (2013.01); *A61B 5/0422* (2013.01); *A61B 5/0432* (2013.01); *A61B 5/4836* (2013.01); *A61B 5/6852* (2013.01); *A61B 6/032* (2013.01);

(Continued)

(58) Field of Classification Search
CPC .................... A61B 5/04005; A61B 5/0402
See application file for complete search history.

(56) References Cited

U.S. PATENT DOCUMENTS

| | | |
|---|---|---|
| 5,555,883 A | 9/1996 | Avitall |
| 5,601,084 A | 2/1997 | Sheehan et al. |

(Continued)

FOREIGN PATENT DOCUMENTS

| | | |
|---|---|---|
| EP | 1166714 | 1/2002 |
| EP | 1760661 | 3/2007 |

(Continued)

OTHER PUBLICATIONS

International Search Report and Written Opinion dated Jun. 26, 2015 issued in International Application No. PCT/US2015/022187.

(Continued)

*Primary Examiner* — Eric D. Bertram
(74) *Attorney, Agent, or Firm* — Onello & Mello, LLP

(57) ABSTRACT

Disclosed are devices, a systems, and methods for determining the dipole densities on heart walls. In particular, a triangularization of the heart wall is performed in which the dipole density of each of multiple regions correlate to the potential measured at various locations within the associated chamber of the heart.

24 Claims, 2 Drawing Sheets

(51) Int. Cl.

| | |
|---|---|
| *A61B 5/02* | (2006.01) |
| *A61B 5/0432* | (2006.01) |
| *A61B 5/00* | (2006.01) |
| *A61B 6/03* | (2006.01) |
| *A61B 8/13* | (2006.01) |
| *A61B 18/02* | (2006.01) |
| *A61B 18/18* | (2006.01) |
| *A61N 7/00* | (2006.01) |
| *A61B 5/044* | (2006.01) |

(52) U.S. Cl.
CPC ............ *A61B 8/13* (2013.01); *A61B 18/0206* (2013.01); *A61B 18/18* (2013.01); *A61N 7/00* (2013.01)

(56) References Cited

U.S. PATENT DOCUMENTS

| | | |
|---|---|---|
| 5,740,808 A | 4/1998 | Panescu et al. |
| 5,795,298 A | 8/1998 | Vesely et al. |
| 6,066,096 A | 5/2000 | Smith et al. |
| 6,187,032 B1 * | 2/2001 | Ohyu ................ A61B 5/04007 600/409 |
| 6,240,307 B1 | 5/2001 | Beatty et al. |
| 6,301,496 B1 | 10/2001 | Reisfeld |
| 6,400,981 B1 | 6/2002 | Govari |
| 6,574,492 B1 | 6/2003 | Ben-Haim et al. |
| 6,640,119 B1 | 10/2003 | Budd et al. |
| 6,716,166 B2 | 4/2004 | Govari |
| 6,728,562 B1 | 4/2004 | Budd et al. |
| 6,826,420 B1 | 11/2004 | Beatty et al. |
| 6,826,421 B1 | 11/2004 | Beatty et al. |
| 6,990,370 B1 | 1/2006 | Beatty et al. |
| 7,289,843 B2 | 10/2007 | Beatty et al. |
| 7,505,810 B2 | 3/2009 | Harlev et al. |
| 7,573,182 B2 | 8/2009 | Savage |
| 7,841,986 B2 | 11/2010 | He et al. |
| 7,918,793 B2 | 4/2011 | Altmann et al. |
| 7,953,475 B2 | 5/2011 | Harlev et al. |
| 8,147,486 B2 | 4/2012 | Honour et al. |
| 8,412,307 B2 | 4/2013 | Willis et al. |
| 8,417,313 B2 * | 4/2013 | Scharf ................ A61B 5/042 600/374 |
| 8,428,690 B2 | 4/2013 | Li et al. |
| 8,512,255 B2 * | 8/2013 | Scharf ................ A61B 5/0422 600/508 |
| 8,700,119 B2 * | 4/2014 | Scharf ................ A61B 5/042 600/374 |
| 8,918,158 B2 * | 12/2014 | Scharf ................ A61B 5/042 600/374 |
| 9,167,982 B2 * | 10/2015 | Scharf ................ A61B 5/042 |
| 9,192,318 B2 * | 11/2015 | Scharf ................ A61B 5/0422 |
| 2002/0128565 A1 | 9/2002 | Rudy |
| 2002/0165441 A1 | 11/2002 | Coleman et al. |
| 2003/0236466 A1 | 12/2003 | Tarjan et al. |
| 2007/0106146 A1 | 5/2007 | Altmann et al. |
| 2008/0009758 A1 | 1/2008 | Voth |
| 2009/0024086 A1 | 1/2009 | Zhang et al. |
| 2009/0131930 A1 | 5/2009 | Gelbart et al. |
| 2009/0264781 A1 * | 10/2009 | Scharf ................ A61B 5/042 600/509 |
| 2010/0298690 A1 | 11/2010 | Scharf |
| 2011/0172658 A1 | 7/2011 | Gelbart et al. |
| 2012/0143298 A1 | 6/2012 | Just et al. |
| 2013/0226017 A1 | 8/2013 | Scharf et al. |
| 2014/0180150 A1 | 6/2014 | Scharf et al. |

FOREIGN PATENT DOCUMENTS

| | | |
|---|---|---|
| EP | 1779787 | 5/2007 |
| EP | 2051625 | 2/2008 |
| EP | 2252203 | 7/2009 |
| WO | 94/06349 | 3/1994 |
| WO | 9905971 | 2/1999 |
| WO | 00/07501 | 2/2000 |
| WO | 2008014629 | 2/2008 |
| WO | 2009090547 | 7/2009 |
| WO | 2011136867 | 11/2011 |
| WO | 2012100185 | 7/2012 |
| WO | 2014036439 | 3/2014 |

OTHER PUBLICATIONS

International Search Report dated Mar. 10, 2015 issued in corresponding International Application No. PCT/US14/54942.

Gupta, et al., "Point of View Cardiac Mapping: Utility or Futility?", Indian Pacing and Electrophysiology Journal, vol. 2, No. 1, Jan. 1, 2002, pp. 20-32.

European SR dated Sep. 29, 2014, issued in European Application No. 13176658.6.

P. Della Bella, Non-Contact Mapping to Guide Catheter Ablation of Untolerated Ventricular Tachycardia, European Heart Journal (2002) 23, p. 742-752.

PCT ISRWO dated Jun. 5, 2014, issued in corresponding PCT Application No. PCT/US2013/057579.

European Office Action dated Apr. 28, 2014, issued in corresponding European Application No. 09 702 094.5-1660.

ISRWO issued on May 20, 2014 in International application No. PCT/US14/15261.

European Office Action dated Feb. 29, 2016, issued in corresponding European Application No. 07 785 075.8-1657.

Van Oosterom A: "Solidifying the solid angle.", 2002, Journal of Electrocardiology 2002, vol. 35 Suppl, pp. 181-192 ISSN: 0022-0736.

Office Action issued on Mar. 9, 2016 in corresponding European Patent Application No. 13176658.6.

Invitation to Pay Additional Fees issued on Jan. 8, 2014 in corresponding International Application No. PCT/US2013/057579.

Office Action issued on Oct. 4, 2013 in corresponding Canadian Patent Application No. 2,659,898.

Pullan et al. "The inverse problem of electrocardiology" Northeastern University Electrical and Computer Engineering, Feb. 23, 2007.

Christoph Scharff et al. Declaration under 37 C.F.R. 1.132, Nov. 15, 2012.

He et al. "An equivalent body surface charge model representing three-dimensional bioelectrical activity" IEEE Transactions on Biomedical Engineering, 42.7 (1995) pp. 637-646.

Partial European Search Report dated Apr. 29, 2014 in corresponding European Application No. 13176658.

International Search Report dated Sep. 10, 2014 issued in corresponding International Application No. PCT/US14/54942.

Examiner's Report Dated Dec. 22, 2015 in related Canadian Application No. 2,656,898.

William G. Stevenson et al: "Recording Techniques for Clinical Electrophysiology", Journal of Cardiovascular Electrophysiology., vol. 16, No. 9, Sep. 1, 2005, pp. 1017-1022.

Wolfgang Nolting: Elektrodynamik—Grundkurs Theoretische Physik 3, Springer Spektrum, p. 89-91.

Office Action issued on Mar. 9, 2016 in corresponding European Patent Application No. 09702094.5.

Office Action issued on Apr. 27, 2016 in corresponding Canadian Application No. 2,747,859.

* cited by examiner

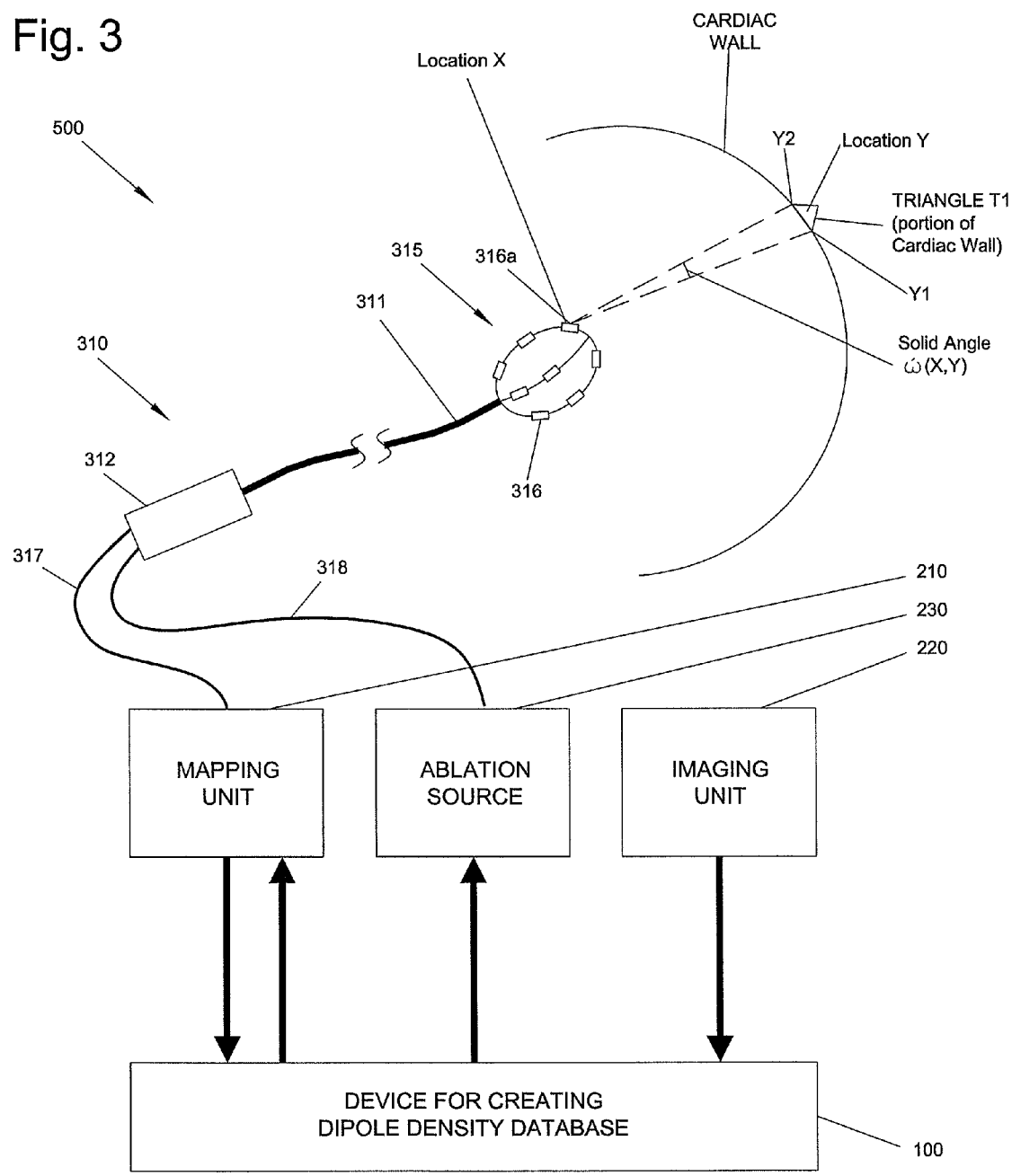

DEVICE AND METHOD FOR THE GEOMETRIC DETERMINATION OF ELECTRICAL DIPOLE DENSITIES ON THE CARDIAC WALL

CROSS REFERENCE TO RELATED APPLICATIONS

The present application is a continuation application of U.S. patent application Ser. No. 13/946,712 filed on Jul. 19, 2013, now U.S Pat. No. 9,192,318 which is a continuation application of U.S. patent application Ser. No. 12/836,411, filed on Jul. 16, 2010, now U.S. Pat. No. 8,512,255, which is a 371 national stage application of Patent Cooperation Treaty Application No. PCT/IB2009/000071 filed Jan. 16, 2009, entitled A DEVICE AND METHOD FOR THE GEOMETRIC DETERMINATION OF ELECTRICAL DIPOLE DENSITIES ON THE CARDIAC WALL, which in turn claims priority to Swiss Patent Application 00068/08 filed Jan. 17, 2008, each of which is incorporated herein by reference.

FIELD OF THE INVENTION

The present invention relates generally to the localization and treatment of cardiac arrhythmias, and more particularly to devices and methods for the geometric determination of electrical dipole densities on the cardiac wall.

BACKGROUND

Systems used to localize the origin of cardiac arrhythmias measure potentials (e.g. in millivolts) in the cardiac chambers and localize them on a three dimensional representation of the cardiac chamber wall. The measurement of the electrical activity present on the cardiac walls is called mapping. For this purpose, a multiple electrode mapping catheter may be positioned within the heart such that multiple potentials can be simultaneously measured at different locations on the wall of the cardiac chamber without having direct wall contact (non-contact mapping). The cardiac chamber is visualized as a three dimensional structure, either directly by moving one or more mapping electrodes within the corresponding heart chamber or by importing an anatomical geometry of the cardiac chamber from an imaging device (e.g. Computed Tomography, MRI, or ultrasound). The electrical activity within the heart can be measured with the multi-electrode mapping catheter, which may be able to simultaneously measure potentials at different points in three dimensional space. In the current systems, the measured potentials from the non-contact multi-electrode mapping catheter do not directly correspond to the electrical activity on the cardiac wall as measured with an electrode with direct wall contact (contact mapping). The measured potentials of the non-contact mapping system have to be converted with computer programs and extrapolated into virtual electrograms projected on the heart chamber of the mapping system.

The current conversion methods are inaccurate, and further processing, termed regularization methods, have to be used. These regularization methods decrease spatial resolution. Another limitation of the current methods is that the provided potentials represent only the mean electrical activity that emanates from different cells, consisting of membranes separating electrical dipoles.

Since the localization of cardiac arrhythmias by the use of potentials is imprecise, the successful treatment of cardiac arrhythmias has been difficult and has demonstrated limited success and reliability. There is, therefore, a need for improved methods of localizing cardiac arrhythmias.

SUMMARY OF THE INVENTION

Several unique devices, systems, and methods for creating a database of dipole densities at a surface of a patient's heart are provided. Dipole density information can be used by a clinician to diagnose and treat heart diseases such as arrhythmias. The dipole density information is based on anatomical models of the patient's heart and mapping information recorded by multiple electrodes, such as electrodes included on the distal end of a three dimensional mapping catheter.

According to a first aspect of the invention, a device for creating a database of dipole densities at the surface of one or more cardiac chambers of a patient is provided. The device includes a first receiver that receives mapping information from multiple electrodes included in one or more mapping catheters. The electrodes are placed in a cardiac chamber of the patient's heart. The device further includes a second receiver that receives anatomical information. The anatomical information may be a generic heart model, or more preferably tissue contour and other anatomical information recorded from the patient's own heart. A dipole density module determines the database of dipole densities, in the table form $d(y)$, where y represents the location on the heart tissue including that particular dipole density. The potential at various locations x, within a cardiac chamber and termed $V(x)$, are recorded by the multiple electrodes. Solid angle $\omega(x,y)$ represents the solid angle for a triangle projection between location x (electrode location in chamber) and y (triangle location on chamber wall). The dipole density module determines the dipole density for individual triangle shaped projections onto the cardiac chamber wall based on the following: each triangle projection at location y contributes $\omega(x,y)$ times the dipole density $d(y)$ to the potential $V(x)$ at the point x.

In a preferred embodiment, the device comprises a software program, e.g., such as a software program loaded onto a personal computer; an ECG system; a cardiac tissue ablation system and/or an imaging system. The number of triangles determined by the dipole density module is sufficiently large (triangle area small enough) such that the dipole density for each triangle projection is relatively constant. Typically 1000 or more triangles are used in the calculations, such as a calculation based on a standard sized Left Atrium. Larger numbers of triangles are used for larger sized chambers.

In another preferred embodiment, the patient is being diagnosed and/or treated for a heart condition, such as an arrhythmia. The electrodes are included at the distal end of one or more mapping catheters and are placed into a chamber of the patient's heart to record potentials. An imaging instrument, such as an instrument that provides a generic model of a heart, or an instrument which provides an anatomical model of the patient's heart, delivers the anatomical information to the second receiver. In a preferred embodiment, the imaging instrument is one or more of: Computed Tomography; MRI; ultrasound; and an ECG system with mapping catheter.

In another preferred embodiment, the dipole density module implements an algorithm configured to assist in the creation of the database of dipole densities. The algorithm may be a progressive algorithm configured to be modified or refined to improve spatial and/or time resolution of the database. The dipole density module may determine a map of dipole densities at corresponding time intervals. A synthesis of maps represents a cascade of activation sequences of each corresponding heart beat.

In another preferred embodiment, the device includes a third receiver. The third receiver receives mapping information from one or more skin electrodes. The dipole density module uses the skin electrode signals to calculate or recalculate the database of dipole densities, using equations listed herebelow.

According to another aspect of the invention, a system for creating a database of dipole densities at the surface of one or more cardiac chambers of a patient's heart is provided. In addition to the device of the present invention, the system includes one or more of a multiple electrode catheter; an imaging instrument; an ablation device; and at least one surface or skin electrode. In a preferred embodiment, the mapping catheter is also used for ablating tissue identified by the database of dipole densities. The system includes a monitor to display the dipole density information, such as information displayed in relative geometry to the chamber of the patient's heart.

According to another aspect of the invention, a method of creating a database of dipole densities at the surface of one or more cardiac chambers of a patient's heart is provided. The method can be used to diagnose and/or treat cardiac disease. In a preferred embodiment, the method is used to diagnose and treat Atrial Fibrillation (AF). In another preferred embodiment, the method is used to detect ventricular ischemia and/or quantify myocardial function. The method includes placing an array of multiple electrodes within a chamber of the patient's heart to measure potentials. The array of multiple electrodes may or may not be repositioned to determine dipole densities.

In another preferred embodiment, the method further includes placing one or more skin electrodes. The information recorded by the skin electrodes is used to determine the database of dipole densities.

BRIEF DESCRIPTION OF THE DRAWINGS

The accompanying drawings, which are incorporated in and constitute a part of this specification, illustrate various embodiments in accordance with the present invention, and, together with the description, serve to explain the principles of the invention. In the drawings:

FIG. 3 illustrates a schematic view of an embodiment of a system for determining a database table of dipole densities of at least one heart chamber with help of the solid angle $\omega(x,y)$, consistent with aspects of the present invention.

DESCRIPTION OF THE EMBODIMENTS

Figure 1:
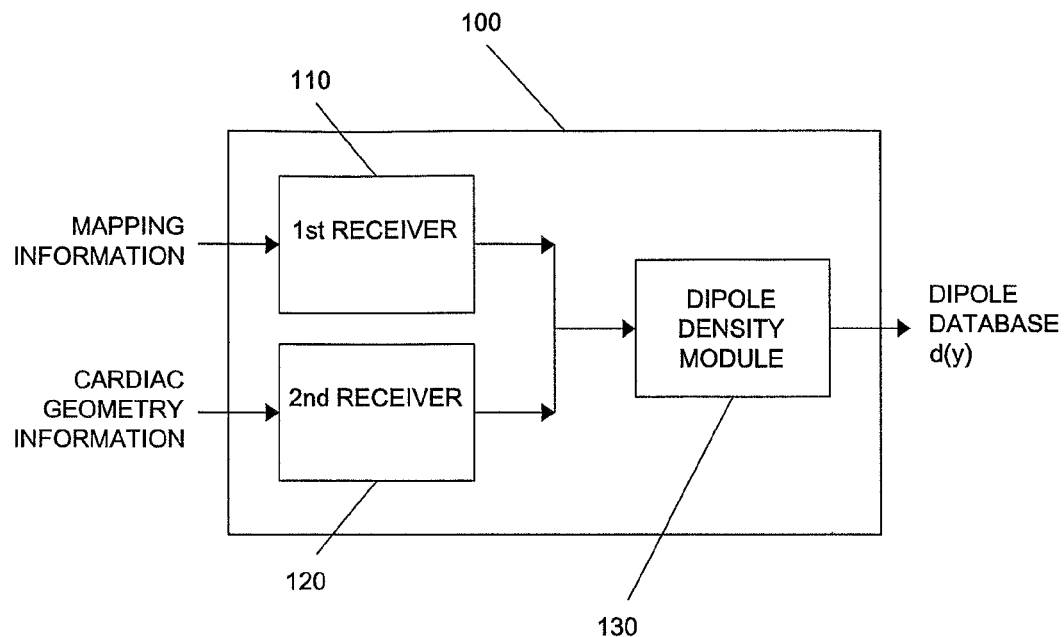
FIG. 1 illustrates a schematic view of an embodiment of a device for determining a database table of dipole densities d(y) of at least one heart chamber, consistent with aspects of the present invention.

Reference will now be made in detail to the embodiments in accordance with aspects of the present invention, examples of which are illustrated in the accompanying drawings. Wherever possible, the same reference numbers will be used throughout the drawings to refer to the same or like parts.

A device for calculating surface charge densities has been described in detail in PCT International Application Number PCT/CH2007/000380 (hereinafter the '380 patent application) naming Scharf as inventor, filed Aug. 3, 2007, and entitled METHOD AND DEVICE FOR DETERMINING AND PRESENTING SURFACE CHARGE AND DIPOLE DENSITIES ON CARDIAC WALLS, and is incorporated by reference herein in its entirety. The present invention provides an improved device, system and method for calculating and visualizing the distribution and activity of dipole charge densities on a cardiac wall. The dipole densities are directly determined geometrically, avoiding the errors encountered using previous extrapolation algorithms.

In accordance with the present invention, provided is a device that measures and calculates a database of dipole densities d(y) on the cardiac wall. The actual measured potentials in the heart result from electrical activity of cells, which can be regarded as dipoles. The dipoles consist of ion charges on both sides of biological membranes. The use of dipole densities offers a precise representation of the electrical activity. Systems and methods in accordance with the present invention efficiently and effectively calculate the dipole densities utilizing one or more mathematical theorems. This calculation is significantly more precise than calculations of virtual potentials produced by current systems, which lose spatial precision because of the required numerical methods and the use of potentials instead of dipole densities. Systems and methods in accordance with the present invention are efficient in calculating dipole densities geometrically, such as through the use of computer systems, or similar microcontroller and/or mathematical processing equipment.

Definitions. To facilitate an understanding of the invention, a number of terms are defined below.

As used herein, the terms "subject" and "patient" refer to any animal, such as a mammal like livestock, pets, and preferably a human. Specific examples of "subjects" and "patients" include, but are not limited, to individuals requiring medical assistance, and in particular, patients with an arrhythmia such as atrial fibrillation (AF).

As used herein, the term "solid angle" is the angle subtended by a triangle on the heart wall at the position x of observation. When viewed from location x, straight lines are drawn from point x to the boundaries of the triangle, and a sphere is constructed of radius r=1 with center of x. The straight lines then define the spherical triangle on the surface of the sphere. The solid angle is proportional to the surface area of the projection of that object onto a sphere centered at the point x.

Figure 2:
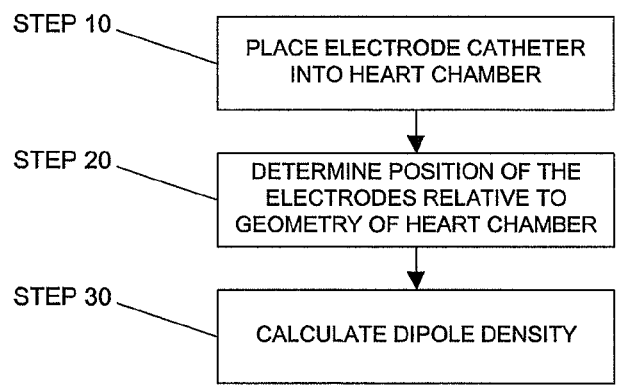
FIG. 2 illustrates a flow chart of an embodiment of a preferred method for determining a database table of dipole densities of at least one heart chamber, consistent with aspects of the present invention.

The methods and devices of the present invention have advantages over previous prior art devices. FIGS. 1-3 illustrate various preferred embodiments of devices, systems and methods in accordance with aspects of the present invention. However, the present invention is not limited to these particular configurations.

Referring now to FIG. 1, a schematic view of an embodiment of a device for determining a database table of dipole densities of at least one heart chamber of a patient is illustrated. Device 100 includes a first receiver 110 configured to receive electrical potentials from a separate device, such as a device including a multi-electrode mapping catheter placed in the circulating blood within a chamber of the patient's heart. Device 100 further includes a second receiver 120 configured to receive cardiac geometry information (e.g. the geometric contour of the cardiac chamber wall), such as from an instrument including, but not limited to: Computed Tomography; MRI; Ultrasound; a multi-electrode mapping catheter; and combinations of these. Alternatively, a standard geometry can be loaded representing a model of the cardiac chamber. Device 100 further includes a dipole density module 130 which comprises mathematical processing element, such as a computer or other electronic module including software and/or hardware for performing mathematical or other calculations. Dipole density module 130 receives mapping information from first receiver 110 and cardiac geometry information from second receiver 120. Dipole density module 130 preferably uses one or more algorithms to process the received mapping and geometry information to produce a database table of dipole densities.

The geometrical model of the cardiac chamber is processed by dipole density module 130 into multiple small triangles (triangularization). When the triangles are sufficiently small, the dipole density at each triangle can be regarded as constant. In a preferred embodiment, a standard cardiac chamber of 4-6 cm diameter is divided up into over 1000 triangles. In another preferred embodiment, the number of triangles determined by dipole density module 130 is based on the size of the heart chamber. With the electrodes positioned in a cardiac chamber by a clinician, such as an electrophysiologist, the potentials at each electrode are recorded. Each triangle is seen by the corresponding electrode under a certain solid angle. The dipole density module 130 computes the solid angle $\omega(x,y)$ subtended by each triangle at position y on each electrode at position x on the multi-electrode catheter. If the dipole density at the triangle is $d(y)$, the triangle contributes $\omega(x,y)$ times $d(y)$ to the potential $V(x)$ at the position x on the multi-electrode catheter. The total measured potential $V(x)$ is the sum resulting from all the triangles. A detailed description is provided in reference to FIG. 3 herebelow.

In a preferred embodiment, dipole density module 130 implements a progressive algorithm that can be modified and/or refined in order to improve spatial and/or time resolution of the database of dipole densities that are produced. The dipole densities $d(y)$ are obtained by solving a linear system of equations. This calculation requires some care to avoid numerical instabilities. Thereby a map of dipole densities can be created at each corresponding time interval. The synthesis of the maps generates a cascade of the activation sequence of each corresponding heart beat that can be used to define the origin of the electrical activity, arrhythmias or diagnose cardiac disease.

The measuring electrodes used in the present invention are placed in the blood flow in a heart chamber, a relatively homogeneous condition, such that the mathematical analysis of the present invention is well applicable. In a preferred embodiment, skin electrodes are also implemented such that dipole density module 130 can use the information received from the skin electrodes to calculate and/or recalculate the dipole densities for the cardiac wall. The spatial resolution which can be obtained by invasive (i.e., placed in the heart chamber) multi-electrode potential measurements is limited by the number of electrodes that can be placed in any cardiac chamber, such as the Left Atrium (LA). Skin placed electrodes, such as electrodes placed on the thorax, are not as space limited. However, due mainly to the inhomogeneous structure of the body, it is difficult to localize the actual sources of the skin electrode measured potentials. A highly complicated boundary value problem must be solved with boundary conditions that are poorly known, and previous attempts at determining the "action potential" from body surface ECG (alone) have not been very successful.

The badly defined boundary value problem can be avoided by an additional measurement (in addition to the skin electrode measurements) of the multi-electrode array of the present invention. A small sinusoidal voltage $V_l$ is applied to each electrode l=1, . . . L on the electrode array in the heart, and the resulting voltages $W_k$, k =1, . . . K is measured at the surface electrodes. This yields the K×L transition matrix $A_{kl}$ $$W_k = \sum_{l=1}^{L} A_{kl} V_l. \tag{1}$$

Calculating solid angles produces the linear transformation $B_{ln}$ between the electrode array potentials $V_l$ and the dipole densities $d_n$, n=1, . . . N of N regions of the heart wall:

$$V_l = \sum_{n=1}^{N} B_{ln} d_n. \tag{2}$$

N is chosen to be N=K+L where K is the number of surface electrodes and L is the number of internally placed array electrodes.

Substituting equation (2) into (1) we have:

$$W_k = \sum_{l=1}^{L} \sum_{n=1}^{N} A_{kl} B_{ln} d_n. \tag{3}$$

Therefore, by simultaneous measuring of the potentials of the cardiac activity with all K+L electrodes, N=K+L dipole densities of N regions on the heart wall can be calculated. This method yields a higher spatial resolution than the L array electrodes alone. In the solution of the linear system of equations (2)+(3), regularization techniques must be used (e.g. Tikhonov regularization and its modifications) in order to avoid numerical instabilities.

Referring now to FIG. 2, an embodiment of a preferred method for determining a database table of dipole densities of at least one heart chamber of a patient is illustrated. In Step 10, a multi-electrode array is placed within the corresponding heart chamber. In Step 20, the geometry of the corresponding heart chamber is obtained in relation to the multi-electrode array position, such as by moving around a second mapping electrode or by importing a geometry model from an imaging study (e.g. using computed tomography, MRI or ultrasound before or after the multi-electrode array of electrodes has been placed in the heart chamber). The surface of the geometry of the corresponding heart chamber is divided into small triangles, typically at least 1000 small triangles.

In Step 30, the dipole density $d(y)$ can be calculated from the measured potential values and the calculated solid angles. The measurements can be repeated successively during the cardiac cycle giving a high timely resolution during each millisecond. The information of the timely dependent dipole densities can be depicted as an activation map of the corresponding heart chamber for the given heart beat. The information can be used to diagnose and/or treat a patient with a cardiac arrhythmia, such as an atrial fibrillation patient.

In a preferred embodiment, the information is used to determine cardiac wall treatment locations for lesion creation, such as a lesion created in the Left or Right atrium, by an RF, ultrasound or cryogenic ablation catheter. In another preferred embodiment, the multiple electrode mapping array is placed in a ventricle and the dipole densities are determined for the ventricular wall, such as to detect ischemia or quantify myocardial function.

Referring now to FIG. 3, an embodiment of a system for determining a database table of dipole densities of at least one heart chamber of a patient is illustrated. System 500 includes device 100, which is configured to create a database table of dipole densities d(y) based on voltage potential measurements within the heart chamber and image information relating to the heart chamber, as has been described hereabove. System 500 further includes imaging unit 220, which is configured to provide a two or three-dimensional image of the heart chamber to device 100. Imaging unit 220 may perform at least one of Computed Tomography, MRI and/or ultrasound imaging. Imaging unit 220 may produce any form of real or virtual models of the cardiac chambers, such that a triangularization analysis is possible.

System 500 further includes mapping catheter 310, which includes shaft 311, shown inserted into a chamber of a patient's heart, such as the Left Atrium (LA). At the distal end of shaft 311 is an electrode array 315 including multiple electrodes 316. Electrode array 315 is shown in a basket construction, but numerous other constructions can be used including multiple independent arms, spiral arrays, electrode covered balloons, and other constructions configured to place multiple electrodes into a three-dimensional space. In a preferred embodiment, any catheter with a three-dimensional array of electrodes can be used to supply the mapping information to device 100.

In this embodiment, electrodes 316 are connected to wires, not shown, but traveling proximally to cable 317, which is electrically connected to a mapping unit 210, such as an electrocardiogram (ECG) unit. ECG unit 210 includes a monitor for displaying information, such as the potentials recorded by electrodes 316, as well as the dipole density information produced by device 100. In an alternative embodiment, device 100 further includes a monitor, not shown, but configured to display one or more of: dipole density information; potentials recorded by electrodes 316; and cardiac chamber contours and other geometry information. In a preferred embodiment, dipole density and or recorded potentials information is shown in reference to a three-dimensional representation of the heart chamber into which catheter 310 is inserted. In an alternative embodiment, imaging unit 220 may include a device configured to create an image of the cardiac chamber from signals recorded from an electrode catheter, such as catheter 310.

System 500 may include a device for treating a cardiac arrhythmia, such as ablation source 230, which is electrically attached to electrodes 316 via cable 318. Alternatively or additionally, ablation source 230 can be attached to a different ablation catheter, such as a single or multiple ablation element catheter configured to deliver ablation energy such as RF energy, cryogenic energy, or other tissue disrupting energy.

As shown in FIG. 3, triangle T1, defined by device 100, is at location Y. Electrode 316a of catheter 310 is at location X. The geometric relationship between triangle T1 and Location X is defined by the solid angle, angle ω(X,Y). Device 100 includes dipole density module 130 such that each triangle at location y contributes ω (x,y) times the dipole density d(y) to the potential V(x) at the position x on a multi-electrode. Solid angle ω(x,y), as defined above, corresponds to the triangle at a location y and the electrode at positions x on the multi-electrode array. The dipole density module 130 of device 100 determines from the total measured potential V(x), which is the sum resulting from all the triangles defined by device 100, the desired dipole density d(y).

When sufficient potentials values V(x) are measured (e.g. from 10 to 10,000 with increasing number of measured potentials providing more accurate results), the dipole density d(y) at many equally distributed regions y on the cardiac wall is calculated by solving a linear equation system. By interpolation of the measured potentials (e.g. with help of splines) their number can be increased to a higher number of regions. The solid angle ω(x,y) of a region is the sum of the solid angles of the individual triangles in the region on the cardiac wall. This calculation of dipole density results, such as via an automatic computer program forming at least part of dipole density module 130.

In a preferred embodiment, the results are presented in a visual, anatomical format, such as depicting the dipole densities on a geometric image of the cardiac wall in relation to time (t). This format allows a clinician, such as an electrophysiologist, to determine the activation sequence on the cardiac wall, such as to determine treatment locations for a cardiac arrhythmia. The results may be shown on a display of mapping unit 210, or on a separate unit such as a display included with device 100, display not shown but preferably a color monitor. In a preferred embodiment, the device of the present invention is implemented as, or includes, a software program that is executable by at least one processor. The software program can be integrated into one or more of: an ECG system; a cardiac tissue ablation system; an imaging system; a computer; and combinations of these.

In a preferred embodiment, the multi-electrode catheter includes at least 10 electrodes, configured to represent a three dimensional body with known geometry. The electrodes are preferably positioned in a spherical geometry, such as a spherical geometry created in a basket catheter. Elliptical electrode array geometries may be used, such as those provided in the Ensite Array Catheter, manufactured by St. Jude Medical of St. Paul Minn. In an alternative embodiment, multiple catheters are inserted into the heart chamber to provide the multiple electrodes.

In an alternative embodiment, the electrodes of the multi-electrode mapping array are repositioned during the method of determining dipole densities. Repositioning of electrodes can be beneficial to increase the number of measured potential values, if electrode positions are known. Therefore, repositioning is in concordance with adjustment of the geometry map in relation to the multi-electrode mapping catheter.

Other embodiments of the invention will be apparent to those skilled in the art from consideration of the specification and practice of the embodiments disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claims set forth herebelow not be construed as being order-specific unless such order specificity is expressly stated in the claim.

We claim:
1. A method of treating a patient, comprising:
   storing a geometrical representation of one or more cardiac chambers in a computer storage media;

sensing and recording a plurality of potentials generated from cardiac activity with multiple electrodes disposed on and/or in a body;

generating with a computer processor a database of dipole densities d(y) associated with one or more surfaces of the one or more cardiac chambers based on the plurality of potentials and the geometrical representation of the one or more cardiac chambers;

diagnosing a cardiac condition based on the database of dipole densities; and treating the cardiac condition based on the database of dipole densities.

2. The method of claim 1, wherein diagnosing the cardiac condition includes:

diagnosing the cardiac condition on cardiac wall tissue of the one or more cardiac chambers based on the database of dipole densities d(y).

3. The method of claim 1, wherein generating the database of dipole densities includes:

mapping the dipole densities to the one or more surfaces of the one or more cardiac chambers.

4. The method of claim 3, further comprising:

generating a computer output of the dipole densities mapped to the one or more surfaces of the one or more cardiac chambers before and after the treating of the cardiac condition.

5. The method of claim 3, further comprising:

updating the database of dipole densities at a plurality of time intervals during the cardiac activity.

6. The method of claim 5, wherein the plurality of time intervals includes at least one time interval per cardiac cycle.

7. The method of claim 6, wherein the plurality of time intervals includes a plurality of time intervals per cardiac cycle.

8. The method of claim 5, wherein the plurality of time intervals includes a time interval of about a millisecond.

9. The method of claim 5, wherein diagnosing the cardiac condition includes:

defining an origin of the cardiac condition from dipole densities taken from a cascade of cardiac activation sequences corresponding to plurality of time intervals.

10. The method of claim 5, further comprising:

generating a computer display of dipole density information based on the database of dipole densities; and updating the computer display of the dipole information based on updating the database of dipole densities.

11. The method of claim 10, wherein:

the computer display includes the mapping of dipole densities to the one or more surfaces of the one or more cardiac chambers at the plurality of time intervals; and updating the computer display comprises updating the mapping of the dipole densities to the one or more surfaces of the one or more cardiac chambers at the plurality of time intervals.

12. The method of claim 11, wherein updating the computer display comprises synthesizing a plurality of dipole density maps taken at different time intervals.

13. The method of claim 1, wherein the database of dipole densities d(y) represents a distribution and activity of dipole charge densities on one or more cardiac wall.

14. The method of claim 1, wherein generating the database of dipole densities d(y) includes projecting geometric shapes onto cardiac walls of the one or more cardiac chambers and determining a dipole density for each projected geometric shape based on the plurality of potentials.

15. The method of claim 1, wherein generating the database of dipole densities includes determining calculated dipole density values by interpolating sensed and recorded potentials V(x).

16. The method of claim 1, wherein generating the database of dipole densities includes moving at least some of the multiple electrodes and producing and/or updating the database of dipole densities based on sensed and recorded potentials before and after such movement.

17. The method of claim 1, wherein diagnosing the cardiac condition includes quantifying myocardial function.

18. The method of claim 1, wherein the cardiac condition is:

a ventricular ischemia;

an arrhythmia; and/or a heart disease.

19. The method of claim 1, wherein the treating of the cardiac condition comprises selecting one or more cardiac wall locations for creation of one or more lesions.

20. The method of claim 19, further comprising delivering energy to create the one or more lesions.

21. The method of claim 20, wherein the delivered energy comprises energy selected from the group consisting of:

RF energy;

ultrasound energy;

cryogenic energy; and combinations thereof.

22. The method of claim 1, wherein storing a geometrical representation of one or more cardiac chambers includes imaging the one or more cardiac chambers.

23. The method of claim 22, wherein imaging the one or more cardiac chambers includes using an imaging technique from a group consisting of:

ultrasound;

computed tomography;

magnetic resonance imaging eletrocardiography ; and combinations thereof.

24. The method of claim 1, wherein sensing and recording the plurality of potentials generated from cardiac activity includes sensing and recording potentials from multiple electrodes within at least one cardiac chamber and at least one skin electrode on the body.

\* \* \* \* \*